United States Patent
Tseti

(10) Patent No.: US 11,786,460 B2
(45) Date of Patent: Oct. 17, 2023

(54) PHARMACEUTICAL DRY POWDER COMPOSITION FOR INHALATION COMPRISING A THYROID HORMONE

(71) Applicant: Ioulia Tseti, Kifissia Attikis (GR)

(72) Inventor: Ioulia Tseti, Kifissia Attikis (GR)

(73) Assignee: Ioulia Tseti, Kifissia Attikis (GR)

( * ) Notice: Subject to any disclaimer, the term of this patent is extended or adjusted under 35 U.S.C. 154(b) by 0 days.

(21) Appl. No.: 17/048,483

(22) PCT Filed: Apr. 10, 2019

(86) PCT No.: PCT/EP2019/059123
§ 371 (c)(1),
(2) Date: Oct. 16, 2020

(87) PCT Pub. No.: WO2019/201712
PCT Pub. Date: Oct. 24, 2019

(65) Prior Publication Data
US 2021/0077391 A1  Mar. 18, 2021

(30) Foreign Application Priority Data
Apr. 16, 2018 (EP) .................................. 18167617
Mar. 22, 2019 (EP) .................................. 19386017

(51) Int. Cl.
| A61K 9/00 | (2006.01) |
| A61K 9/14 | (2006.01) |
| A61K 47/26 | (2006.01) |
| A61K 31/198 | (2006.01) |

(52) U.S. Cl.
CPC ............ *A61K 9/0075* (2013.01); *A61K 9/145* (2013.01); *A61K 31/198* (2013.01); *A61K 47/26* (2013.01)

(58) Field of Classification Search
None
See application file for complete search history.

(56) References Cited

U.S. PATENT DOCUMENTS

| 6,183,782 | B1 | 2/2001 | Hallworth | |
| 6,955,824 | B1 | 10/2005 | Hallworth | |
| 8,333,192 | B2 | 12/2012 | Tseti | |
| 2003/0007932 | A1* | 1/2003 | Bechtold-Peters | A61P 43/00 424/46 |
| 2004/0033259 | A1 | 2/2004 | Hanshew, Jr. et al. | |
| 2004/0171550 | A1* | 9/2004 | Backstrom | A61K 9/145 424/85.2 |
| 2006/0292083 | A1 | 12/2006 | Zeng | |
| 2008/0178870 | A1 | 7/2008 | Tseti | |
| 2016/0143855 | A1 | 5/2016 | Kannan et al. | |

FOREIGN PATENT DOCUMENTS

| CO | 08002797 | 5/2008 |
| JP | H05306235 A | 11/1993 |
| JP | 2004-502708 A | 1/2004 |
| JP | 2005-507881 A | 3/2005 |
| WO | 95/00127 A1 | 1/1995 |
| WO | 2002/03914 A | 1/2002 |
| WO | 2003/024396 A2 | 3/2003 |
| WO | 2005046636 A1 | 5/2005 |
| WO | 2007009913 | 1/2007 |
| WO | 2007070851 A1 | 6/2007 |
| WO | 2011120779 A1 | 10/2011 |
| WO | 2012028745 A1 | 3/2012 |

OTHER PUBLICATIONS

Peng, "Influence of physical properties of carrier on the performance of dry powder inhalers", Acta Parmaceutica Sinica B, 6(4), pp. 308-318, 2016 (Year: 2016).*
Buttini et al., "Particles and Powders: Tools of Innovation for Non-Invasive Drug Administration", Journal of Controlled Release 161 (2012) 693-702.
Horiba Scientific "Pharmaceutical Aerosol Applications" Jul. 2, 2019, 2 pages.
International Search Report and Written Opinion issued in International Application No. PCT/EP2019/059123, dated Jul. 11, 2019, 14 pages.
Rahimpour et al., "Alternative Carriers in Dry Powder Inhaler Formulations" Drug Discovery Today, vol. 19, No. 5, May 2014, pp. 618-626.
Wikipedia Page—Reduzierende Zucker, dated Aug. 11, 2018, 2 pages.

* cited by examiner

*Primary Examiner* — Robert T. Crow
*Assistant Examiner* — John P Nguyen
(74) *Attorney, Agent, or Firm* — Dilworth IP, LLC

(57) ABSTRACT

The invention relates to dry powder compositions, suitable for inhalation through an appropriate inhalation device, comprising a thyroid hormone drug and a non-reducing sugar or sugar alcohol as a single carrier. The preparations of the invention show higher stability than the corresponding ones with lactose monohydrate, a commonly used carrier for dry powder preparations.

5 Claims, No Drawings

PHARMACEUTICAL DRY POWDER COMPOSITION FOR INHALATION COMPRISING A THYROID HORMONE

The invention concerns stable thyroid hormone drug compositions with a non-reducing sugar or sugar alcohol as a single carrier, selected from trehalose, raffinose, mannitol and isomaltitol, free of any other excipients, in the form of dry powder, suitable for inhalation through an appropriate inhalation device. The preparations of the invention show higher stability than the corresponding ones with the commonly used carrier for dry powder preparations, lactose monohydrate.

BACKGROUND OF THE INVENTION

A search for prior art revealed some documents which may be considered relevant for the present case. However, upon closer inspection of these documents it turned out that these documents as discussed in the following are not relevant.

JP H05 306235 A discloses lyophilized compositions comprising a para-thyroid hormone as active ingredient in conjunction with an effective amount of sugars and sodium chloride. The sugar may be mannitol or trehalose. However, a para-thyroid hormone is both structurally and functionally different from thyroid hormones such as levothyroxine and liothyronine. Para-thyroid hormone is an 84 amino acid polypeptide that regulates extra cellular calcium homeostasis. Moreover, this patent application clearly notes that only the combined use of a saccharide and sodium chloride may provide the appropriate stability of the lyophilized composition. It is further noted in this document that with a sugar alone a decreased stability is observed. Anyway, this document does not even remotely relate to inhalation. Lyophilized compositions as disclosed in this document are intended for reconstitution in an aqueous medium to form an injectable preparation. Such lyophilized compositions are neither intended nor suitable for inhalation.

US 2004/0033259 A1 cited in U.S. Pat. No. 8,333,192 B2 concerns a storage-stable dosage form of a thyroxine active drug composition. Levothyroxine sodium is the preferred active drug substance, mannitol is the preferred alditol present in the composition and sucrose is the preferred saccharide. Anyway, the preferred preparation is a compressed tablet. Alternatively, the preparation may be used to fill capsules. However, there is no reference to any preparation that is useful or may be used as a powder for inhalation. The only reference to powders in this document concerns the production of dosage forms such as tablets or solid-filled capsules.

US 2016/0143855 A1 relates to pharmaceutical compositions comprising a thyroid hormone drug. The pharmaceutical composition may comprise further at least one carbohydrate, in particular a saccharide, and one or more pharmaceutically acceptable excipients (see claim 1). Although this document refers to powders as a solid dosage form, there is no reference to inhalation preparations. A skilled person, however, is knowledgeable that not any powder is suitable for inhalation to the respiratory system. The performance of a powder suggested for inhalation is strongly dependent from physical properties of carrier particles, such as their particle size, morphology and shape.

U.S. Pat. No. 8,333,192 B2 relates to a device comprising an inhaler suitable for administration of a stable dry powder blend, which contains a blend comprising a thyroid hormone drug, in particular levothyroxine sodium, and other additives such as lactose particles, sodium starch glycolate, magnesium stearate, and talc silicified.

Example 14 of this US patent refers to a dry powder composition comprising mannitol, sucrose, microcrystalline cellulose, and magnesium stearate. At the outset, this is clearly not a composition suitable for inhalation. Components, such as microcrystalline cellulose, FD& C yellow Aluminum Lake and magnesium stearate are certainly not suitable or intended for inhalation. Moreover, example 14 gives no information as regards the particle size of the active ingredients. Moreover, there is no mention of any solid carrier. Thus, the composition of example 14 cannot be considered as a pharmaceutical dry powder composition suitable for inhalation.

In summary, the teaching of these documents cannot be relevant for preparations concerning a dry powder thyroid hormone drug and a non-reducing sugar or sugar alcohol as the single carrier for inhalation purposes.

It is well known that approximately 60-80% of levothyroxine is absorbed after oral administration mainly in the jejunum and ileum. Absorption is maximal on an empty stomach; therefore, it is standard practice to ask patients to consume levothyroxine on an empty stomach at least half to 1 h before food or other medications. Administration through inhalation would minimize the potential for undesirable interactions between levothyroxine with other drugs or food, thus increasing its bioavailability. In vitro permeability studies on Calu-3 cells indicated that levothyroxine can be absorbed effectively from the respiratory mucosa. Moreover, levothyroxine shows high potency and is therapeutically effective in the microgram range and therefore is suitable for pulmonary absorption compared to orally administered drugs. Advantages of the pulmonary route also include a very large absorptive surface area (~80-140 $m^2$), decreased metabolism and efflux transporter activity compared to the oral route, avoidance of first pass effect and potential for rapid onset of action.

Lactose is commonly used in dry powders for inhalation because it is highly crystalline and has satisfactory flow properties. However, lactose is a reducing sugar which makes it incompatible with drugs that have primary amine moieties like the thyroid hormones, namely, levothyroxine and liothyronine. Therefore, it is necessary to develop a dry powder composition presenting high uniformity and stability, being suitable for inhalation that overcomes the above obstacle. Surprisingly, it was found that the dry powdered compositions comprising of a thyroid hormone drug and a single carrier among of the non-reducing sugars/sugar alcohols, trehalose, raffinose, mannitol, isomaltitol, in the absence of any other excipient, antioxidant or preservative, show superior stability than the corresponding compositions based on lactose monohydrate.

DESCRIPTION OF THE INVENTION

According to the invention, a thyroid hormone drug is diluted in a solid carrier to form a dry powder mixture that is fluidized when the subject (patient) inhales. The thyroid hormone drug is one of levothyroxine or liothyronine or their salts or a mixture of them. The solid carrier is selected among the non-reducing sugars/sugar alcohols trehalose, raffinose, mannitol and/or isomaltitol.

According to the invention, the thyroid hormone drug is in the form of a micronized powder with an average particle size between 1 and 10 micrometers or 2 and 5 micrometers. The particle size reduction of the active ingredient to the aforementioned extent enhances the overall performance of the dry powder composition in order to be suitable for inhalation. Larger particles usually deposit in the oral cavity or pharynx, from which they are easily cleared, while smaller particles may not deposit at all or settle very slowly. Accordingly, the carrier particle size is selected to be in the range of 20 to 400 micrometers or 40 to 200 micrometers, in order to enhance the flow and reduce aggregation during the delivery of the active ingredient to the lungs.

The measurement of particle size (i.e. average particle size) as required by the present invention is well known to the skilled person. Typically, the particle size analysis was conducted using a laser diffraction particle size analyzer (i.e. an Analysette 22 Laser-Particle Sizer from Fritsch GmbH). The volume mean diameter and other particle size parameters (D10%, D50% and D90%) were calculated automatically using the software provided. Approximately 200-300 mg of a sample was dispersed in purified water and filled in the measuring cell. The particle size measurement was carried out under stirring condition during the experiment. The results are the mean and standard deviation of five determinations.

Thus, the present invention concerns a pharmaceutical dry powder composition consisting of a micronized powder of a thyroid hormone with an average particle size between 1 and 10 micrometer, diluted in solid carrier particles of a size in the range of 20 to 400 micrometer, suitable for inhalation, wherein the thyroid hormone drug is one of levothyroxine or liothyronine or their salts, comprising as a single carrier a non-reducing sugar or sugar alcohol and absent of any other excipient, antioxidant or preservative.

According to a particular aspect of the present invention, a pharmaceutical dry powder composition comprises a micronized powder of a thyroid hormone with an average particle size between 1 and 10 micrometer and solid carrier particles of a size in the range of 20 to 400 micrometer, wherein the carrier particles are made up of non-reducing sugars or sugar alcohols. Preferably, the pharmaceutical dry powder composition essentially—or optionally only—consists of the micronized powder of the thyroid hormone and the solid carrier particles. In a preferred embodiment, the thyroid drug hormone is levothyroxine, liothyronine or a pharmaceutically acceptable salt thereof. The non-reducing sugar may be selected from sucrose, trehalose, raffinose, stachyose and verbascose. The non-reducing sugar alcohol may be selected from mannitol and isomaltitol.

According to the invention, the preparation comprising of 5-500 or 10-400 micrograms of the thyroid hormone drug and 99.995-99.950 or 99.990-99.600 mg of the solid carrier. Accordingly, the amount of the thyroid hormone drug represents the 0.005-0.5% or 0.01-0.4% of the dry powder composition, while the amount of the solid carrier represents the 99.500-99.995% or 99.600-99.990% of the dry powder composition.

According to the invention, the dry powder compositions prepared following a geometric dilution process. First, the micronized thyroid hormone drug is placed in an isolator where the necessary quantity is weighted and mixed with an equal amount of the solid carrier. The two-powder blend is triturated and finely grinded, until it is completely mixed. Subsequently, an amount of the remaining carrier equal to that in the pestle is added and the trituration process is repeated. This process is repeated until the entire amount of carrier is combined with the mixture. The final dry blend stored in amber glass tightly sealed vials and analyzed as per its homogeneity and levothyroxine assay.

The invention is further described in the following non-limiting representative examples.

Example 1

The following example refers to a process preparing a dry powder composition comprising of levothyroxine sodium and trehalose. The preparation of the dry powder composition took place in a rotating bin placed in an isolator. 0.100 mg of Levothyroxine sodium hydrate and 0.100 mg of trehalose are placed in the bin and mixed for 10 min at 15 rpm. Then, 0.200 mg of carrier was added in the bin and the blend is mixed for 10 min at 15 rpm. Then, 0.400 mg of trehalose was added in the bin and the blend is mixed for 10 min at 15 rpm. Then, 0.800 mg of trehalose was added in the bin and the blend is mixed for 10 min at 15 rpm. Then, 1.600 mg of trehalose was added in the bin and the blend is mixed for 10 min at 15 rpm. Then, 3.200 mg of trehalose was added in the bin and the blend is mixed for 10 min at 15 rpm. Then, 13.333 mg of trehalose was added in the bin and the blend is mixed for 10 min at 15 rpm. Then, 33.333 mg of trehalose was added in the bin and the blend is mixed for 10 min at 15 rpm. Then, 46.934 mg of trehalose was added in the bin and the blend is mixed for 10 min at 15 rpm. The final dry blend stored in amber glass tightly sealed vials and analyzed as per its homogeneity (blend uniformity) and levothyroxine assay. The blend uniformity was determined by measuring the levothyroxine assay in the aid of high-performance liquid chromatography (HPLC), in samples collected from 10 different places of the bin. A stability study is undertaken after long-term storage (18 months) under normal conditions (25±2° C./60±5% RH), following a testing protocol of a 6 month time interval.

Example 2

The following example refers to a process preparing a dry powder composition comprising of levothyroxine sodium and raffinose. The preparation of the dry powder composition took place in a rotating bin placed in an isolator. 0.100 mg of Levothyroxine sodium hydrate and 0.100 mg of raffinose are placed in the bin and mixed for 10 min at 15 rpm. Then, 0.200 mg of carrier was added in the bin and the blend is mixed for 10 min at 15 rpm. Then, 0.400 mg of raffinose was added in the bin and the blend is mixed for 10 min at 15 rpm. Then, 0.800 mg of raffinose was added in the bin and the blend is mixed for 10 min at 15 rpm. Then, 1.600 mg of raffinose was added in the bin and the blend is mixed for 10 min at 15 rpm. Then, 3.200 mg of raffinose was added in the bin and the blend is mixed for 10 min at 15 rpm. Then, 13.333 mg of raffinose was added in the bin and the blend is mixed for 10 min at 15 rpm. Then, 33.333 mg of raffinose was added in the bin and the blend is mixed for 10 min at 15 rpm. Then, 46.934 mg of raffinose was added in the bin and the blend is mixed for 10 min at 15 rpm. The final dry blend stored in amber glass tightly sealed vials and analyzed as per its homogeneity (blend uniformity) and levothyroxine assay. The blend uniformity was determined by measuring the levothyroxine assay in the aid of high-performance liquid chromatography (HPLC), in samples collected from 10 different places of the bin. A stability study is undertaken after long-term storage (18 months) under normal conditions (25±2° C./60±5% RH), following a testing protocol of a 6 month time interval.

Example 3

The following example refers to a process preparing a dry powder composition comprising of levothyroxine sodium and mannitol. The preparation of the dry powder composition took place in a rotating bin placed in an isolator. 0.100 mg of Levothyroxine sodium hydrate and 0.100 mg of mannitol are placed in the bin and mixed for 10 min at 15 rpm. Then, 0.200 mg of carrier was added in the bin and the blend is mixed for 10 min at 15 rpm. Then, 0.400 mg of mannitol was added in the bin and the blend is mixed for 10 min at 15 rpm. Then, 0.800 mg of mannitol was added in the bin and the blend is mixed for 10 min at 15 rpm. Then, 1.600 mg of mannitol was added in the bin and the blend is mixed for 10 min at 15 rpm. Then, 3.200 mg of mannitol was added in the bin and the blend is mixed for 10 min at 15 rpm. Then, 13.333 mg of mannitol was added in the bin and the blend is mixed for 10 min at 15 rpm. Then, 33.333 mg of mannitol was added in the bin and the blend is mixed for 10 min at 15 rpm. Then, 46.934 mg of mannitol was added in the bin and the blend is mixed for 10 min at 15 rpm. The final dry blend stored in amber glass tightly sealed vials and analyzed as per its homogeneity (blend uniformity) and levothyroxine assay. The blend uniformity was determined by measuring the levothyroxine assay in the aid of high-performance liquid chromatography (HPLC), in samples collected from 10 different places of the bin. A stability study is undertaken after long-term storage (18 months) under normal conditions (25±2° C./60±5% RH), following a testing protocol of a 6 month time interval.

Example 4

The following example refers to a process preparing a dry powder composition comprising of levothyroxine sodium and isomaltitol. The preparation of the dry powder composition took place in a rotating bin placed in an isolator. 0.100 mg of Levothyroxine sodium hydrate and 0.100 mg of isomaltitol are placed in the bin and mixed for 10 min at 15 rpm. Then, 0.200 mg of carrier was added in the bin and the blend is mixed for 10 min at 15 rpm. Then, 0.400 mg of isomaltitol was added in the bin and the blend is mixed for 10 min at 15 rpm. Then, 0.800 mg of isomaltitol was added in the bin and the blend is mixed for 10 min at 15 rpm. Then, 1.600 mg of isomaltitol was added in the bin and the blend is mixed for 10 min at 15 rpm. Then, 3.200 mg of isomaltitol was added in the bin and the blend is mixed for 10 min at 15 rpm. Then, 13.333 mg of isomaltitol was added in the bin and the blend is mixed for 10 min at 15 rpm. Then, 33.333 mg of isomaltitol was added in the bin and the blend is mixed for 10 min at 15 rpm. Then, 46.934 mg of isomaltitol was added in the bin and the blend is mixed for 10 min at 15 rpm. The final dry blend stored in amber glass tightly sealed vials and analyzed as per its homogeneity (blend uniformity) and levothyroxine assay. The blend uniformity was determined by measuring the levothyroxine assay in the aid of high-performance liquid chromatography (HPLC), in samples collected from 10 different places of the bin. A stability study is undertaken after long-term storage (18 months) under normal conditions (25±2° C./60±5% RH), following a testing protocol of a 6 month time interval.

A comparative example (Example 5) performed to prepare a dry powder composition of Levothyroxine sodium with the commonly used inhalation carrier lactose monohydrate, following the method of the invention. In this context, the preparation of the dry powder composition took place in a rotating bin placed in an isolator. 0.100 mg of Levothyroxine sodium hydrate and 0.100 mg of lactose monohydrate are placed in the bin and mixed for 10 min at 15 rpm. Then, 0.200 mg of carrier was added in the bin and the blend is mixed for 10 min at 15 rpm. Then, 0.400 mg of lactose monohydrate was added in the bin and the blend is mixed for 10 min at 15 rpm. Then, 0.800 mg of lactose monohydrate was added in the bin and the blend is mixed for 10 min at 15 rpm. Then, 1.600 mg of lactose monohydrate was added in the bin and the blend is mixed for 10 min at 15 rpm. Then, 3.200 mg of lactose monohydrate was added in the bin and the blend is mixed for 10 min at 15 rpm. Then, 13.333 mg of lactose monohydrate was added in the bin and the blend is mixed for 10 min at 15 rpm. Then, 33.333 mg of lactose monohydrate was added in the bin and the blend is mixed for 10 min at 15 rpm. Then, 46.934 mg of lactose monohydrate was added in the bin and the blend is mixed for 10 min at 15 rpm. The final dry blend stored in amber glass tightly sealed vials and analyzed as per its homogeneity (blend uniformity) and levothyroxine assay. The blend uniformity was determined by measuring the levothyroxine assay in the aid of high-performance liquid chromatography (HPLC), in samples collected from 10 different places of the bin. A stability study is undertaken after long-term storage (18 months) under normal conditions (25±2° C./60±5% RH), following a testing protocol of a 6 month time interval.

TABLE 1

| Dry powder compositions described in Examples 1-5. | | | | | |
|---|---|---|---|---|---|
| Ingredient (Mean particle size) | Example 1 | Example 2 | Example 3 | Example 4 | Example 5 |
| Levothyroxine Sodium Hydrate (2.39 µm) | 0.100 mg | 0.100 mg | 0.100 mg | 0.100 mg | 0.100 mg |
| Trehalose (64 µm) | 99.900 mg | — | — | — | — |
| Raffinose (88 µm) | — | 99.900 mg | — | — | — |
| Mannitol (100 µm) | — | — | 99.900 mg | — | — |
| Isomaltitol (41 µm) | — | — | — | 99.900 mg | — |
| Lactose monohydrate (48 µm) | — | — | — | — | 99.900 mg |

It is within the ability of a skilled person to proceed on the preparation of dry powder mixtures of different strengths of thyroid hormone drug by following the procedure described in Examples 1-4 and mixing the appropriate amounts of a selected carrier.

The homogeneity of the blend was determined by measuring the levothyroxine assay in the aid of high-performance liquid chromatography (HPLC), in samples collected from 10 different places of the bin. All compositions showed high homogeneity suggesting that the compositions are suitable to be used for inhalation.

TABLE 2

Blend uniformity of Levothyroxine dry powder compositions (100 μg/100 mg)

| | Levothyroxine Assay (%) | | | | |
|---|---|---|---|---|---|
| Sample | Example 1 | Example 2 | Example 3 | Example 4 | Example 5 |
| 1 | 102.2 | 104.8 | 99.1 | 99.2 | 102.5 |
| 2 | 101.5 | 104.1 | 100.2 | 99.2 | 103.3 |
| 3 | 99.9 | 103.9 | 98.8 | 97.9 | 103.5 |
| 4 | 101.9 | 104.9 | 99.5 | 97.8 | 102.1 |
| 5 | 102.2 | 104.7 | 98.2 | 97.1 | 103.0 |
| 6 | 102.8 | 105.2 | 99.2 | 97.2 | 103.0 |
| 7 | 101.8 | 105.4 | 98.9 | 101.1 | 103.7 |
| 8 | 102.3 | 105.9 | 98.7 | 101.5 | 103.1 |
| 9 | 102.5 | 104.8 | 99.5 | 101.5 | 103.0 |
| 10 | 101.7 | 105.3 | 99.2 | 100.9 | 102.6 |
| Average | 101.9 | 104.9 | 99.1 | 99.3 | 103.0 |
| SD | 0.80 | 0.60 | 0.54 | 1.78 | 0.48 |
| RSD | 0.78 | 0.57 | 0.55 | 1.79 | 0.47 | where SD: Standard Deviation, RSD: Relative Standard Deviation

Levothyroxine sodium dry powder compositions of Examples 1-4 stored in tightly sealed amber glass vials for 18 months under normal conditions, namely at 25±2° C. and 60±5% relative humidity and the stability of the dry powder studied in terms of levothyroxine assay (%) and impurity profile. The stability results compared to those obtained from a corresponding dry powder composition of Levothyroxine sodium with lactose monohydrate (Comparative Example 5) which stored under the same conditions of temperature and relative humidity.

Dry powder composition of Levothyroxine sodium with trehalose showed a 3.2% potency loss of Levothyroxine Sodium after 18 months storage at 25±2° C./60±5% relative humidity, which is significantly superior compared to the 13.6% potency loss of levothyroxine assay of the levothyroxine dry powder with lactose monohydrate.

TABLE 3

Stability studies of Levothyroxine Sodium dry powder compositions

| Levothyroxine Sodium Dry Powder Composition | | Levothyroxine assay (%) Storage Conditions: 25 ± 2° C./60 ± 5% RH | | | |
|---|---|---|---|---|---|
| Example | Carrier | t = 0 | 6 months | 12 months | 18 months |
| Example 1 | Trehalose | 101.9 | 100.6 | 99.9 | 98.7 |
| Example 2 | Raffinose | 104.9 | 103.8 | 102.7 | 101.1[5] |
| Example 3 | Mannitol | 99.1 | 97.3 | 96.3 | 94.9 |
| Example 4 | Imaltitol | 99.3 | 98.4 | 96.4 | 94.7 |
| Example 5 | Lactose monohydrate | 103.0 | 96.6 | 93.9 | 89.4 |

Impurity profile of Levothyroxine dry powder compositions of the invention after 18 months storage at 25±2° C./60±5% RH verifies the superiority of the dry powder levothyroxine sodium composition with the carriers trehalose, raffinose, mannitol and isomaltitol compared to lactose monohydrate. The composition with lactose monohydrate shows a high percentage of unspecified impurities (4.4%) probably due to the adduct formation between levothyroxine and lactose.

TABLE 4

Impurity Profile of Levothyroxine dry powder compositions after 18 months storage at 25 ± 2° C./60 ± 5% RH.

| Impurity | Example 1 | Example 2 | Example 3 | Example 4 | Example 5 |
|---|---|---|---|---|---|
| Liothyronine (%) | 0.17 | 0.16 | 0.21 | 0.24 | 0.82 |
| TETRAC (%) | 0.08 | 0.10 | 0.11 | 0.15 | 0.19 |
| T4-Benzoic acid (%) | 0.09 | 0.11 | 0.13 | 0.19 | 0.25 |
| Total Other Unspecified Impurities (%) | 0.58 | 0.64 | 0.78 | 0.91 | 4.4 |
| Total Impurities (%) | 0.92 | 1.01 | 1.23 | 1.49 | 5.66 |

I claim:

1. A pharmaceutical dry powder composition consisting of:
   a micronized powder of a thyroid hormone drug selected from levothyroxine, liothyronine or their salts; and
   a single solid carrier absent of any other excipient, antioxidant or preservative, selected from a non-reducing sugar or a non-reducing sugar alcohol, the non-reducing sugar being selected from sucrose, trehalose, raffinose, stachyose or verbascose, and the non-reducing sugar alcohol being selected from mannitol or isomaltitol,
   wherein the powder of the thyroid hormone drug, having an average particle size between 1 and 10 micrometer, is diluted in particles of the single solid carrier having a size in the range of 20 to 400 micrometer suitable for inhalation.

2. The pharmaceutical dry powder composition according to claim 1, wherein the composition comprises from 0.005% to 0.5% w/w of the thyroid hormone drug.

3. The pharmaceutical dry powder composition according to claim 1, wherein the composition comprises from 99.500% to 99.995% w/w of the carrier.

4. The pharmaceutical dry powder composition according to claim 1 wherein the composition comprises from 99.500% to 99.995% w/w of the carrier.

5. The pharmaceutical dry powder composition according to claim 2 wherein the composition comprises from 99.500% to 99.995% w/w of the carrier.

* * * * *